US009492096B2

(12) United States Patent
Brockway et al.

(10) Patent No.: US 9,492,096 B2
(45) Date of Patent: Nov. 15, 2016

(54) ECG SENSING APPARATUSES, SYSTEMS AND METHODS

(71) Applicant: VivaQuant LLC, St. Paul, MN (US)

(72) Inventors: Brian Brockway, St. Paul, MN (US); Marina Brockway, St. Paul, MN (US)

(73) Assignee: VivaQuant LLC, St. Paul, MN (US)

( * ) Notice: Subject to any disclaimer, the term of this patent is extended or adjusted under 35 U.S.C. 154(b) by 0 days.

(21) Appl. No.: 14/467,957

(22) Filed: Aug. 25, 2014

(65) Prior Publication Data

US 2014/0364756 A1 Dec. 11, 2014

Related U.S. Application Data

(63) Continuation-in-part of application No. 14/305,927, filed on Jun. 16, 2014, now Pat. No. 9,008,762, which is a continuation-in-part of application No. 14/230,439, filed on Mar. 31, 2014, now Pat. No.
(Continued)

(30) Foreign Application Priority Data

Feb. 5, 2013 (WO) ................ PCT/US2013/024770

(51) Int. Cl.
A61B 5/04 (2006.01)
A61B 5/0456 (2006.01)
(Continued)

(52) U.S. Cl.
CPC ......... A61B 5/04012 (2013.01); A61B 5/0006 (2013.01); A61B 5/0245 (2013.01); A61B 5/04017 (2013.01); A61B 5/0452 (2013.01); A61B 5/0456 (2013.01); A61B 5/04087 (2013.01); A61B 5/7253 (2013.01); A61B 7/00 (2013.01); G06F 17/14 (2013.01); G06K 9/0051 (2013.01); G06K 9/0053 (2013.01); G06F 19/3431 (2013.01)

(58) Field of Classification Search
None
See application file for complete search history.

(56) References Cited

U.S. PATENT DOCUMENTS 5,090,418 A 2/1992 Squires et al.
5,521,851 A 5/1996 Wei et al.
(Continued)

FOREIGN PATENT DOCUMENTS

EP 1553869 A1 7/2005
WO 2013/043157 A2 3/2013

OTHER PUBLICATIONS

B. Widrow, et al., "Adaptive noise cancelling: principles and applications," IEEE Proc., vol. 63, No. 12, pp. 1692-1716, Dec. 1975.
(Continued)

Primary Examiner — Brian T Gedeon
(74) Attorney, Agent, or Firm — Crawford Maunu PLLC

(57) ABSTRACT

Aspects of the present disclosure are directed to processing ECG signals from a subject. As may be implemented in accordance with one or more embodiments, respective electrodes sense ECG signals from a subject, and the ECG signals are digitized and processed, such as to remove noise, detect a QRS complex, evaluate quality, detect arrhythmia and/or to store the signals. In response to an input from the subject, one or more of the ECG signals is recorded along with sound from the user, such as to concurrently record the user's voice for describing conditions in connection with the recording of the ECG signals. This approach can be carried out in an enclosed housing, operated adjacent the subject's thorax. The processed digitized ECG signals and the audio signals are then communicated for receipt by an external device.

32 Claims, 6 Drawing Sheets

Related U.S. Application Data 9,072,438, said application No. 14/230,439 is a continuation of application No. 13/668,898, filed on Nov. 5, 2012, now Pat. No. 8,688,202, which is a continuation-in-part of application No. PCT/US2011/052371, filed on Sep. 20, 2011, and a continuation-in-part of application No. 12/938,995, filed on Nov. 3, 2010, now Pat. No. 8,632,465, said application No. 13/668,898 is a continuation-in-part of application No. 13/172,415, filed on Jun. 29, 2011, now Pat. No. 8,433,395, which is a continuation-in-part of application No. 12/938,995, filed on Nov. 3, 2010, now Pat. No. 8,632,465, said application No. 13/668,898 is a continuation-in-part of application No. 13/931,228, filed on Jun. 28, 2013, which is a continuation-in-part of application No. 13/092,530, filed on Apr. 22, 2011, now Pat. No. 8,478,389.

(60) Provisional application No. 61/869,250, filed on Aug. 23, 2013, provisional application No. 61/944,253, filed on Feb. 25, 2014, provisional application No. 61/257,718, filed on Nov. 3, 2009, provisional application No. 61/366,052, filed on Jul. 20, 2010, provisional application No. 61/359,462, filed on Jun. 29, 2010, provisional application No. 61/370,026, filed on Aug. 2, 2010, provisional application No. 61/555,165, filed on Nov. 3, 2011.

(51) Int. Cl.

| | |
|---|---|
| *A61B 5/00* | (2006.01) |
| *A61B 7/00* | (2006.01) |
| *A61B 5/0245* | (2006.01) |
| *A61B 5/0408* | (2006.01) |
| *A61B 5/0452* | (2006.01) |
| *G06F 17/14* | (2006.01) |
| *G06K 9/00* | (2006.01) |
| *G06F 19/00* | (2011.01) |

(56) References Cited

U.S. PATENT DOCUMENTS

| | | | |
|---|---|---|---|
| 5,792,065 | A | 8/1998 | Xue et al. |
| 5,817,027 | A | 10/1998 | Arand et al. |
| 5,827,195 | A | 10/1998 | Lander |
| 5,987,352 | A | 11/1999 | Klein et al. |
| 6,389,308 | B1 | 5/2002 | Shusterman |
| 6,589,189 | B2 | 7/2003 | Meyerson et al. |
| 6,690,959 | B2 | 2/2004 | Thompson |
| 6,701,170 | B2 | 3/2004 | Stetson |
| 6,822,564 | B2 | 11/2004 | Al-Ali |
| 6,881,191 | B2 | 4/2005 | Oakley et al. |
| 7,096,060 | B2 | 8/2006 | Arand et al. |
| 7,115,096 | B2 | 10/2006 | Siejko et al. |
| 7,236,819 | B2 | 6/2007 | Brockway et al. |
| 7,272,265 | B2 | 9/2007 | Kouri et al. |
| 7,376,453 | B1 | 5/2008 | Diab et al. |
| 7,627,369 | B2 | 12/2009 | Hunt |
| 7,672,717 | B1 | 3/2010 | Zikov et al. |
| 7,840,259 | B2 | 11/2010 | Xue et al. |
| 8,086,304 | B2 | 12/2011 | Brockway et al. |
| 8,201,330 | B1 | 6/2012 | Rood et al. |
| 8,214,007 | B2 | 7/2012 | Baker et al. |
| 8,271,073 | B2 | 9/2012 | Zhang et al. |
| 8,348,852 | B2 | 1/2013 | Bauer et al. |
| 8,449,469 | B2 * | 5/2013 | Banet .................. A61B 5/021 600/438 |
| 8,460,189 | B2 | 6/2013 | Libbus et al. |
| 8,478,389 | B1 | 7/2013 | Brockway et al. |
| 8,639,319 | B2 | 1/2014 | Hugh et al. |
| 9,037,477 | B2 * | 5/2015 | Bardy .................. A61B 5/0006 705/2 |
| 2004/0167417 | A1 * | 8/2004 | Schulhauser ........ A61B 5/0006 600/513 |
| 2005/0010120 | A1 | 1/2005 | Jung et al. |
| 2005/0101875 | A1 * | 5/2005 | Semler ............... A61B 5/04085 600/509 |
| 2005/0234361 | A1 | 10/2005 | Holland |
| 2005/0283090 | A1 | 12/2005 | Wells |
| 2007/0219453 | A1 | 9/2007 | Kremliovsky et al. |
| 2007/0219455 | A1 | 9/2007 | Wong et al. |
| 2007/0260151 | A1 | 11/2007 | Clifford |
| 2007/0265508 | A1 | 11/2007 | Sheikhzadeh-Nadjar |
| 2008/0065158 | A1 | 3/2008 | Ben-Ezra et al. |
| 2008/0097537 | A1 | 4/2008 | Duann et al. |
| 2008/0183093 | A1 | 7/2008 | Duann et al. |
| 2008/0195169 | A1 * | 8/2008 | Pinter .................. A61B 5/0424 607/28 |
| 2008/0200832 | A1 | 8/2008 | Stone |
| 2009/0069703 | A1 | 3/2009 | Takla et al. |
| 2009/0222262 | A1 | 9/2009 | Kim et al. |
| 2012/0165691 | A1 | 6/2012 | Ting et al. |
| 2012/0197144 | A1 | 8/2012 | Christ et al. |
| 2012/0232417 | A1 | 9/2012 | Zhang |
| 2013/0109937 | A1 | 5/2013 | Banet et al. |
| 2014/0005988 | A1 | 1/2014 | Brockway |

OTHER PUBLICATIONS

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982). (Copy Unavailable).

G. Moody, W. Muldrow, and R. Mark, "A noise stress test for arrhythmia detectors," Computers in Cardiology, pp. 381-384 (1984). (Copy Unavailable).

K. R. Rao and P. Yip, "Discrete Cosine Transform: Algorithms, Advantages, Applications," San Diego, CA: Academic (1990). (Copy Unavailable).

J. Woods. Subband Coding, Kluwer Academic Press (1990). (Copy Unavailable).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993 (Copy Unavailable).

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455. (Copy Unavailable).

Y. Xu, J. Weaver, D. Healy, Jr. And J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

(56) References Cited

OTHER PUBLICATIONS

A. Bell and T. Sejnowski, "An Information-Maximization Approach to Blind Separation and Blind Deconvolution," Neural Computation, 7:1129-1159. (1995).
M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).
V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).
J. Francois Cardoso, "Infomax and Maximum Likelihood for Source Separation," IEEE Letters on Signal Processing, vol. 4, No. 4, pp. 112-114 (Apr. 1997).
M. L. Hilton, "Wavelet and Wavelet Packets Compression of Electrocardiogram," IEEE Transactions on Biomedical Engineering, vol. 44, No. 5, pp. 394-402 (May 1997).
A. Hyvärinen, "New Approximations of Differential Entropy for Independent Component Analysis and Projection Pursuit," In Advances in Neural Information Processing Systems, vol. 10, pp. 273-279, MIT Press. (1997).
W. Sweldens. The lifting scheme: A construction of second generation wavelets. SIAM J. Math. Anal., 29(2):511-546, 1997.
American National Standard ANSI/AAMI EC57:1998, Testing and Reporting Performance Results of Cardiac Rhythm and ST Segment Measurement Algorithms. (Copy Unavailable).
Testing and reporting performance results of cardiac rhythm and ST-segment measurement algorithms ANSI/AAMI EC57:1998. (Copy Unavailable).
L. Torres-Pereira, et. al. "A Biotelemetric Heart Sound Monitoring System," in Proceedings of the 14th International Symposium on Biotelemetry. Marburg, 1998. (Copy Unavailable).
A. Hyvärinen, "Fast and Robust Fixed-Point Algorithms for Independent Component Analysis," IEEE Transactions on Neural Networks, vol. 10, No. 3, pp. 626-634 (May 1999).
J.-F. Cardoso, "High-Order Contrasts for Independent Component Analysis," Neural Comput., vol. 11, No. 1, pp. 157-192 (1999).
S. Chen, D Donoho, and M. Saunders, "Atomic Decomposition by Basis Pursuit," SIAM J. Scientific Computing, vol. 20, No. 1, pp. 33-61 (1999).
Q. Pan, L. Zhang, G. Dai and H. Zhang, "Two Denoising Methods by Wavelet Transform," IEEE Trans. on SP, vol. 47, No. 12, pp. 3401-3406 (Dec. 1999).
G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).
S. Mallat, "A Wavelet Tour of Signal Processing," Academic Press, 1999. (Copy Unavailable).
Langley, P.; Di Bernardo, D.; Murray, A.; Comparison of three measures of QT dispersion. Computers in Cardiology 1999 pp. 69-72 (Copy Unavailable).
Goldberger Al et al. PhysioBank, PhysioToolkit, and PhysioNet: components of a new research resource for complex physiologic signals. Circulation 101(23): e215-e220, Jun. 13, 2000 (Copy Unavailable).
Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).
M. Marcellin, M. gormish, A. Bilgin and M. Boleik, "An Overview of JPEG-2000," Proc. Of IEEE Data Compression Conference, pp. 523-541 (2000).
L. K. Saul and J. B. Allen, "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.
C. Taswell, "The What, How, and Why of Wavelet Shrinkage Denoising," Computing in Science and Engineering, vol. 2, No. 3, pp. 12-19 (2000).
J. S. Richman and J. R. Moorman, Physiological time-series analysis using approximate entropy and sample entropy Am. J. Physiol. 278, H2039 (2000). (Copy Unavailable).
K. Sayood, "Introduction to Data Compression," Academic Press 2000. (Copy Unavailable).
Malik M, Batchvarov VN. Measurement, interpretation and clinical potential of QT dispersion. J Am Coll Cardiol. Nov. 15, 2000;36(6):1749-66.
A. Hyvärinen and E. Oja, "Independent Component Analysis: Algorithms and Applications," Neural Networks, 13(4-5), pp. 411-430 (2000).
R. Mayerburg. Sudden cardiac death: exploring the limits of our knowledge. Journal of Cardiovascular Electrophysiology, vol. 12, No. 3, Mar. 2001 (Copy Unavailable).
M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.
D. Donoho and X. Huo, "Uncertainty Principles and Ideal Atomic Decomposition," IEEE Transactions on Information Theory, vol. 47, No. 7, pp. 2845-2862 (Nov. 2001).
M. Zibulevsky and B. Pearlmutter, "Blind Source Separation by Sparse Decomposition in a Signal Dictionary," Neural Computation. vol. 13, pp. 863-882 (2001).
Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1 (Copy Unavailable).
M. Costa, A. L. Goldberger, and C.-K. Peng, Multiscale Entropy Analysis of Complex Physiologic Time Series, Phys. Rev. Lett. 89, 6, (2002).
B. U. Kohler, C. Hennig, R. Orglmeister. The principles of software QRS detection. IEEE Engineering in Medicine and Biology Magazine, vol. 21, No. 1. (2002), pp. 42-57.
Kellermann, et al.,"A mobile phone based alarm system for supervising vital parameters in free moving rats," BMC Research Notes 2012, 5:119, Feb. 23, 2012.
http://www.simplehelp.net/2006/09/12/how-to-set-up-outlook-2003-for-email/.
Vos, et al. "The Opus Codec," (USAAES 135th Convention, New York, USA, 2013 Oct. 17, 2013).
G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).
T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).
D A Clunie, "Extension of an open source DICOM toolkit to support SCP-ECG waveforms," 2nd OpenECG Workshop 2004, Berlin, Germany.
J.-P. Martinez, et. al., "A wavelet-based ECG delineator: Evaluation on standard databases," IEEE transactions on biomedical engineering, vol. 51, No. 4, pp. 57 (2004).
Thomsen, M. B., Verduyn, S. C., Stengl, M., Beekman, J. D., de Pater, G., van Opstal, J., et al. (2004). Increased short-term variability of repolarization predicts d-sotalolinduced torsade de pointes in dogs. Circulation, 110, 2453-2459.
Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.
Madalena Costa.et. al. Multiscale entropy analysis of biological signals. Physical Review E 71, 021906 s2005d. (Copy Unavailable).
M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

(56) References Cited

OTHER PUBLICATIONS

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).
Hamlin RL. Non-drug-related electrocardiographic features in animal models in safety pharmacology. J Pharmacol Toxicol Methods. Jul.-Aug. 2005; 52(1): 60-76.
HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177. (Copy Unavailable).
R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).
M. Blanco-Velasco, B. Weng and KE Barner, "A New ECG Enhancement Algorithm for Stress ECG Tests," Computers in Cardiology, vol. 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.-M Poggi, "Multivariate de-noising using wavelets and principal component analysis," Computational Statistics & Data Analysis, 50, pp. 2381-2398 (2006).
Aharon, M. Elad and a. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology. vol. 5, pp. 667-677. 2006.
Irian, O.T.; Giovangrandi, L.; Kovacs, G.T.A.; Robust Neural-Network-Based Classification of Premature Ventricular Contractions Using Wavelet Transform and Timing Interval Features, IEEE Transactions on Biomedical Engineering vol. 53, Issue: 12 , , pp. 2507-2515 (Copy Unavailable).
L. Smith, A tutorial on Principal Components Analysis.
Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766 (Copy Unavailable).
K. Oweiss, A. Mason, Y. Suhail, A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).
X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).
R Schimpf, Ch Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008; 5(2): 241-245. (Copy Unavailable).
Sarkar S, Ritscher D, Mehra R. A detector for a chronic implantable atrial tachyarrhythmia monitor. IEEE Trans Biomed Eng. Mar. 2008;55(3):1219-24. (Copy Unavailable).
M. Malik, K. Hnatkova, T. Novotny, G Schmidt Subject-specific profiles of QT/RR hysteresis. Am J Physiol Heart Circ Physiol 295:H2356-H2363, 2008.
Akturk, A. and Goldsman, N. (2008) "Electron transport and full-band electron phonon interactions in graphene" J. Of Applied Physics 103. (Copy Unavailable).
S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008. (Copy Unavailable).
R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).
O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).
H. Li, R. Li, F. Wang. Multiresolution Subband Blind Source Separation: Models and Methods. Journal of Computers, vol. 4, No. 7 (2009), 681-688 (Copy Unavailable).
Afonso, V.X.; Tompkins, W.J.; Detecting ventricular fibrillation. IEEE Engineering in Medicine and Biology Magazine, vol. 14 , Issue: 2, pp. 152-159 (Copy Unavailable).
Dash S, Chon KH, Lu S, Raeder EA. Automatic real time detection of atrial fibrillation. Ann Biomed Eng. Sep. 2009;37(9):1701-9. Epub Jun. 17, 2009. (Copy Unavailable).
M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).
R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).
J. Piccini, et al, Predictors of sudden cardiac death change with time after myocardial infarction: results from the VALIANT trial. European Heart Journal (2009) (Copy Unavailable).
J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).
S. Hadei, M. Iotfizad. A family of adaptive filter algorithms in noise cancellation for speech enhancement. International Journal of Computer and Electrical Engineering, vol. 2, No. 2, Apr. 2010. 1793-8163 (Copy Unavailable).
Allen, M., Tung, V., Kaner, R. (2010) " Honey Carbon: A Review of Graphene" Chem. Rev. 110:132-145. (Copy Unavailable).
Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.
HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454 (Copy Unavailable).
Daubechies I., et al. Synchrosqueezed wavelet transforms: an empirical mode decomposition-like tool. Applied and Computational Harmonic Analysis, vol. 30, Issue 2, Mar. 2011, pp. 243-261 (Copy Unavailable).
M. Brockway and R Hamlin, "Evaluation of an algorithm for highly automated measurements of QT interval," Journal of Pharmacological and Toxicological Methods, vol. 64, pp. 16-24 (2011) (Copy Unavailable).
http://www.physionet.org/physiobank/database/#ecg.
http://www.physionet.org/physiobank/database/mitdb/.

(56) References Cited

OTHER PUBLICATIONS

Tsalaile, et al. "Blind Source Extraction of Heart Sound Signals From Lung Sound Recordings Exploiting Periodicity of the Heart Sound," ICASSP 2008 IEEE, p. 461-464.

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.

* cited by examiner

Figure 1 – System Diagram

Figure 3
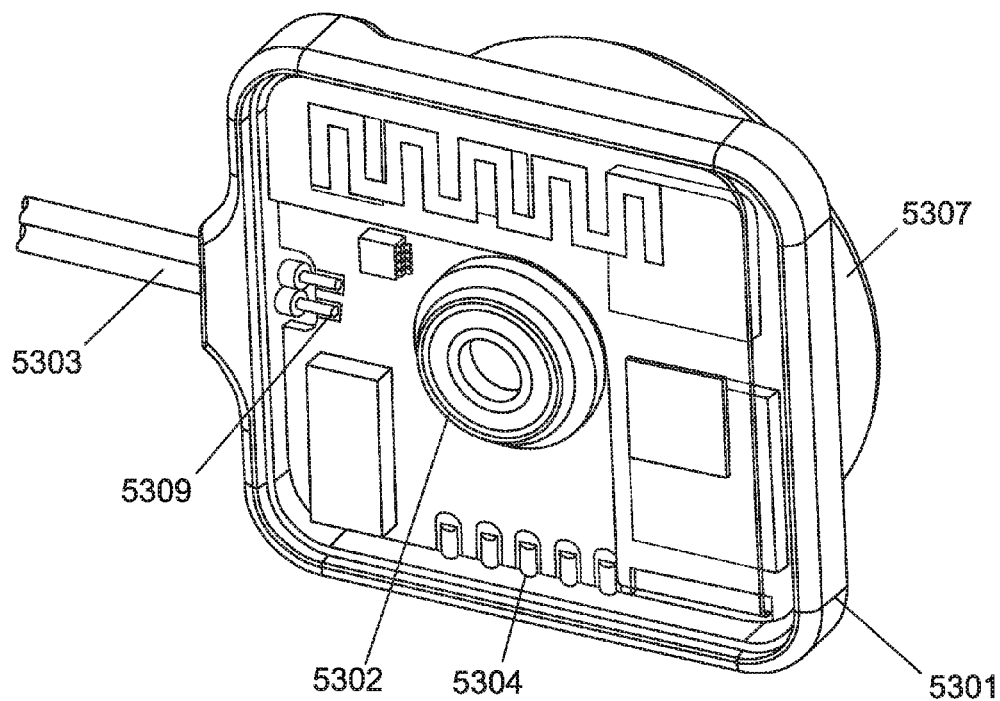
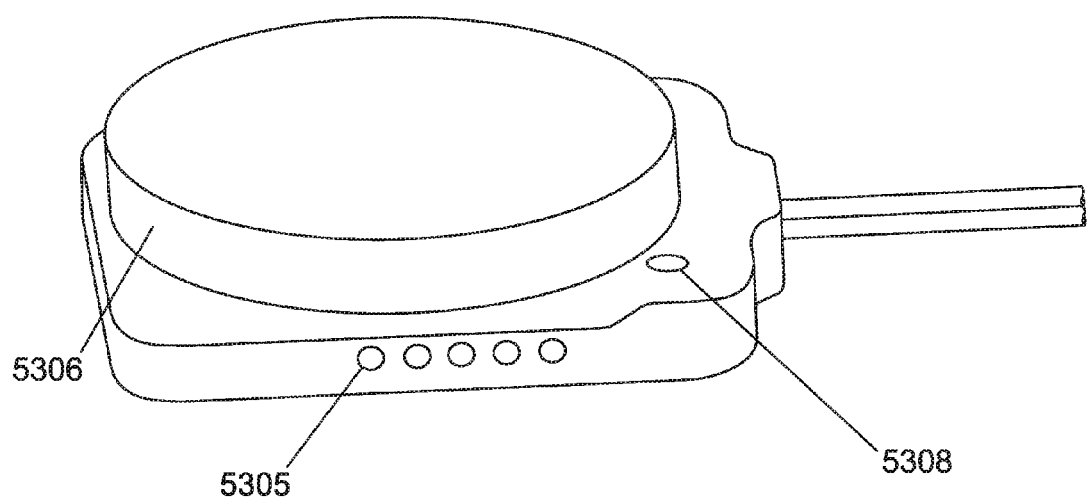

ECG SENSING APPARATUSES, SYSTEMS AND METHODS

FIELD

The present disclosure relates to a system for monitoring ECGs of ambulatory animals and human beings.

BACKGROUND

External wireless devices are often used to monitor ECG in humans and animals for clinical care and in research studies. For example, ambulatory devices that measure electrocardiogram are routinely used to assess arrhythmias in human clinical studies and for diagnosis of the status of patients that may be at risk of arrhythmias. Correlation of symptom and rhythm is often a goal of such evaluations, but limitations of current devices often preclude the ability to do so. Ambulatory monitoring devices often include a button that the patient or a care provider presses when symptoms occur. Pressing the button then results in an event mark in the recording. Patients or care providers are advised to keep a diary that describes the nature of the symptoms. Some devices may include a computer aided function intended to simplify recording of the nature of the symptoms. For example, some devices have a menu displayed on a touch screen that allows the patient to select a description of the symptoms from among a list. Whether a diary or a computer-aided tool is used, a low percentage of patients provide a record of the symptoms associated with an event mark. This limits the ability to correlate symptoms and rhythm and hence reduces the potential diagnostic utility of the system.

Another limitation of current devices is that they must be removed prior to bathing or showering in order to avoid damage from fluid ingress. The devices can be damaged due to exposure to fluid for any reason including falling in the water, exposure to heavy rain, or accidentally leaving a device in a pocket of a garment during washing. This limitation not only creates an inconvenience for the patient but also can result in damage to the device and subsequent expense for the patient, care provider, supplier, or insurer.

Yet another limitation of current device is that measurement of long-vector ECGs (i.e. where at least one electrode is located separate from the electronics housing at a distance of at least 10 cm) often requires the use of a relatively expensive connector and cable harness that can constitute a significant portion of the cost of an ambulatory device.

SUMMARY

Various aspects of the present disclosure are directed to devices, methods and systems for ambulatory monitoring of ECG, in a manner that addresses challenges and limitations including those discussed above.

In accordance with one or more embodiments, an apparatus includes first and second electrodes operable to sense ECG signals from a subject, a digitizing circuit that receives and digitizes the ECG signals sensed by the electrodes, and an audio circuit that captures sound from the subject and converts the sound into electrical audio signals. The apparatus also includes a processing circuit that operates with the electrodes and the digitizing circuit to digitize the ECG signals and process each digitized ECG signal by one or more of removing noise from the digitized ECG signal, storing the digitized ECG signal in a memory circuit, detecting a QRS complex in the digitized ECG signal, evaluating quality of the digitized ECG signal, and detecting arrhythmia in the digitized ECG signal. An input circuit operates to receive an input from the subject, with the processing circuit and audio circuit being respectively operable to initiate recording of at least one of the ECG signals and the sound in response to the input. A communication circuit communicates the processed digitized ECG signals and the audio signals for receipt by an external device.

Another embodiment is directed to an apparatus also having first and second electrodes that sense ECG signals from a subject, a digitizing circuit that digitizes each sensed ECG signal, and an audio circuit that captures sounds from the subject and converts the sounds into electrical audio signals. A wireless communication circuit wirelessly transmits data to an external device. An input device is arranged to receive a tactile input from the subject and to convert the tactile input to an input signal. One or more processors are responsive to each input signal by recording a digitized ECG signal sensed from the subject via the electrodes, and recording the subject's voice via the audio circuit. The processor(s) processes the digitized ECG signal by one or more of removing noise from the digitized ECG signal, storing the digitized ECG signal in a memory circuit, detecting a QRS complex in the digitized ECG signal, evaluating quality of the digitized ECG signal, and detecting arrhythmia in the digitized ECG signal. The recorded voice and digitized ECG signal are wirelessly transmitted to the external device via the wireless communication circuit, thereby providing access to ECG signals and the subject's voice as recorded in conjunction with each ECG signal recorded in response to tactile input from the subject. A power supply provides power to the digitizing circuit, the audio circuit, the communication circuit, the input device, and the processor(s). The input device, audio circuit, communication circuit, power supply and processor(s) are within a housing, and a mechanical support structure supports the housing proximate the subject's thorax.

Another embodiment is directed to a method as follows. ECG signals are sensed from a subject via first and second electrodes, the ECG signals sensed by the electrodes are received and digitized at a digitizing circuit, and sounds are captured from the subject using an audio circuit, with the sounds being converted into electrical audio signals. In a processing circuit operable with the electrodes and digitizing circuit, the ECG signals are digitized and each digitized ECG signal is processed by one or more of: removing noise from the digitized ECG signal, storing the digitized ECG signal in a memory circuit, detecting a QRS complex in the digitized ECG signal, evaluating quality of the digitized ECG signal, and detecting arrhythmia in the digitized ECG signal. In response to receiving an input from the subject via an input circuit, at least one of the ECG signals and the sound are recorded via the processing circuit and the audio circuit. Each processed digitized ECG signal and a corresponding one of the audio signals are communicated, via a communication circuit, for receipt by an external device.

The above summary is not intended to describe each embodiment or every implementation of the present disclosure. The figures and detailed description that follow more particularly exemplify various embodiments.

DESCRIPTION OF THE FIGURES

Various example embodiments may be more completely understood in consideration of the following detailed description in connection with the accompanying drawings, in which:

FIG. 3 shows oblique lower and upper views of an apparatus for detecting ECG and audio signals, incorporated in a housing, in accordance with another example embodiment;

Figure 1:
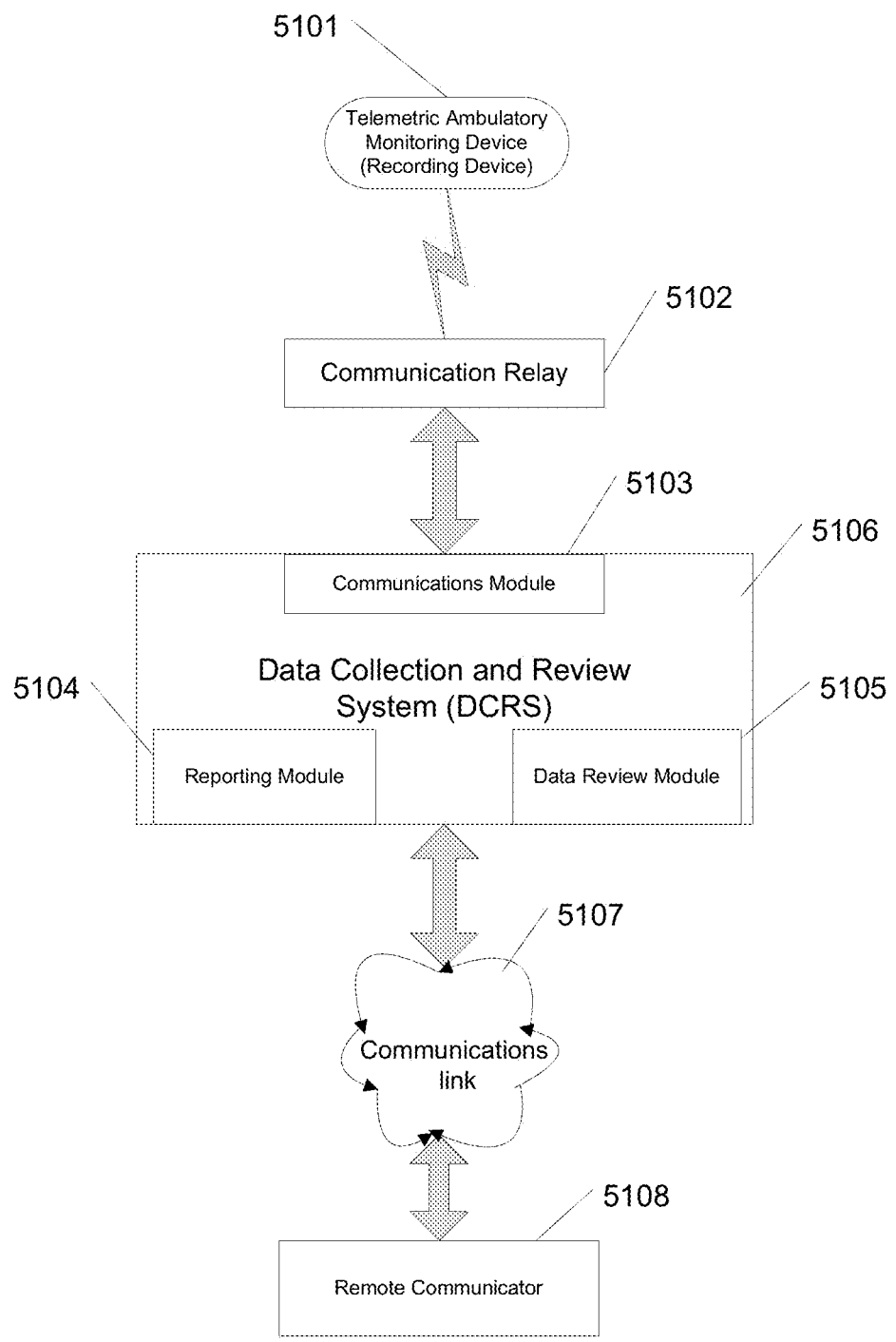
FIG. 1 shows an apparatus worn by a human or animal subject and operable for measuring, processing and recording an ECG, in accordance with an example embodiment.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present invention relate to a system for monitoring, reviewing, and reporting of cardiac status on ambulatory subjects. In the context of this invention, cardiac status may include one or more of the following: incidence of arrhythmias, interval measurements, heart rate variability, metrics of cardiac risk such as a cardiac repolarization characteristic (e.g. T-wave alternans), and electromechanical decoupling. Various embodiments are directed to monitoring human or animal subjects using the device as part of a clinical evaluation while others are directed to human or animal subjects involved in a research study. In connection with certain embodiments, the accuracy of information provided is improved under a broad range of use scenarios, battery life can be extended, the size of monitoring devices can be reduced, and information can be obtained more efficiently. While the present invention is not necessarily limited to such applications, various aspects of the invention may be appreciated through a discussion of examples using this context.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

In accordance with other embodiments, an apparatus includes two or more electrodes, a digitizing circuit coupled to digitize ECG signals sensed from a subject (e.g., a patient) by the electrodes and an audio circuit (e.g., including a microphone) that captures and converts sound into electrical audio signals. The apparatus also includes a processor, an input circuit and a communication circuit. The processor operates to process each digitized ECG signal in one or more of a variety of manners, such as by removing noise, detecting a QRS complex or arrhythmia in the ECG signal, evaluating quality of the ECG signal, or simply storing the ECG signal. The processor is also responsive to an input from subject, such as obtained via the press of a button or a switch, by initiating the recording of at least one of the ECG signals and the sound in response to the input. In this context, the subject's voice can be recorded in connection with an ECG from the subject, based on the subject's input. For instance, when the subject detects or feels an abnormal condition, he or she can depress a button that initiates such a recording. This recording may be carried out from ongoing sensing, and as such may involve recording a time window that begins before the input is provided, and extends after the input (e.g., where the apparatus is operating in a continuous detection mode and stores information for a short time period). The processed digitized ECG signals and the audio signals can then be communicated via a communication circuit, such as a wireless circuit, for receipt by an external device.

The recordings can thus be attributed to one another, permitting a remote medical service provider to evaluate the ECG signals in connection with the subject's voice, which can help to explain a situation relevant to the recording. Such an approach is useful for evaluating cardiac incidents that the subject may feel, or to record an ECG in connection with certain activity (e.g., when a user begins or alters exercise, an ECG may be recorded in connection with the particular exercise being carried out). In some embodiments, the apparatus includes a memory circuit, with the processor being operative to store data that represents and links each ECG signal with sound recorded in connection therewith.

The ECG signals are processed in a variety of manners, to suit particular embodiments. In certain embodiments, the processor provides an indication that at least one of the electrodes is disconnected based on a determined quality of the signal, and enters a low power mode in response to the disconnection. In some embodiments, the signal quality of the ECG signal is evaluated by decomposing the digitized ECG signal into subcomponents, computing a statistical variance of the subcomponents over a time interval, and assessing signal quality based upon the statistical variance of the subcomponents. In other embodiments, noise is removed from the ECG signal by decomposing the signal into subcomponents, identifying a location of the QRS complex of a cardiac cycle in the ECG signal, identifying a first time window in the cardiac cycle that includes the QRS complex, and identifying at least one time window in the cardiac cycle that does not include the QRS complex. For each of the identified time windows, target subcomponents are identified as subcomponents that contain more energy that is within a band of frequencies characteristic of a desired ECG signal in the time window than energy that is outside the band of frequencies characteristic of the desired ECG signal. A denoised physiological signal is then constructed using two or more of the identified target subcomponents.

In some embodiments, the apparatus also includes a transducer that generates audible sound, and the processor audibly communicates an indication of the ECG signal. For instance, where the processor evaluates signal quality of the digitized ECG signal, the audible communication can be generated to provide an indication of the quality. Such an approach may also be used, for example, to alert a subject that one of the electrodes has disconnected.

In various embodiments, one or more of the circuits is included within a housing, which can be placed near the subject's thorax. In some embodiments, the housing includes the digitizing circuit, audio circuit, processing circuit and communication circuit. The housing may be constructed primarily of a non-conductive material and have one or more conductive pins embedded into the non-conductive material, for connection to the electrodes. ECG signals can thus be passed into the housing through the conductive pin(s), which permits processing of the signals while also ensuring that fluid or other components do not pass into (or out of) the housing. In various embodiments, it has been discovered that, by processing signals as discussed herein (e.g., for noise removal or quality evaluation involving subcomponents), such a housing can be made quite small and operated readily via a relatively small battery, which can permit comfortable attachment of the housing to a subject or otherwise near a subject's thorax (e.g., via a fastener or a lanyard type material as discussed herein) for long-term use.

In a more particular embodiment involving a housing such as above, the apparatus also includes a fastener that mechanically supports the housing proximate the subject's thorax. In some implementations, the fastener includes one or more of the electrodes and adheres to the subject's skin. In some implementations, the housing includes a conductive snap at an outer surface and the fastener includes a conductive snap that mates with the conductive snap in the housing. The snaps provide both mechanical support for the housing and electrical connection from the first electrode to the digitizing circuit contained within the housing. In another implementation, a conductive lead wire extends through the housing and a conductive snap is connected to the conductive lead wire. In this implementation, the fastener includes a conductive snap that mates with the conductive snap connected to the conductive lead wire, and provides both mechanical support for the housing and electrical connection from the first electrode to the digitizing circuit contained within the housing.

Another embodiment is directed to an apparatus also having electrodes, a digitizing circuit and an audio circuit that captures sounds and converts sounds into electrical audio signals. The apparatus also includes a wireless communication circuit that wirelessly transmits data to an external device. An input device senses and converts a tactile input (e.g., touch) to an input signal, which is used as a cue in response to which a digitized ECG signal and the subject's voice are recorded. Such an input may involve, for example, a user's depression of a switch or pressure on two switches on opposite sides of a housing, the latter of which may serve to prevent false recordings. A power supply provides power to the digitizing circuit, the audio circuit, the communication circuit, the input device, and the processor(s). The apparatus may further include memory, with the processor operable to store sets of data in the memory circuit where each set of data represents and links a recorded ECG signal with sound recorded in response to the input signal. Recorded voice and ECG signals are wirelessly transmitted to an external device, thereby providing access to ECG signals and the subject's voice as recorded in conjunction with each ECG signal recorded in response to the tactile input.

One or more of the input device, audio circuit, communication circuit, power supply and processor(s) are within a housing. The housing may include non-conductive material as above, and can be implemented with a conductor passing through the housing in a manner that mitigates or prevents liquids or gas from passing into the housing. A mechanical support structure supports the housing proximate the subject's thorax (e.g., an elastic member that encircles at least a portion the thorax and holds one or more of the electrodes in contact with the skin, a loop or band that encircles the subject's thorax, or a lanyard that encircles the subject's neck).

Certain embodiments also employ a transducer as above, which may be within the housing or as part of a housing, positioned to deliver audio to the subject. For instance, where arrhythmia is detected in the digitized ECG signal, the subject can be notified that an arrhythmia has occurred and prompted to verbally describe symptoms by generating sound via the transducer.

In this embodiment, as with the above discussion, the processor or processors can be implemented in a variety of manners, to carry out one or more of a variety of operations upon the digitized ECG signals. In some implementations, operations related to storage, noise removal, detection of a QRS complex or arrhythmia, or evaluating quality via statistical variance are carried out. One or more of these approaches may involve decomposition into subcomponents as discussed above. In some implementations involving the determination of a statistical variance via subcomponents as above, the disconnection of one or more electrodes is detected based upon a ratio of the statistical variance of a subset of the subcomponents to total statistical variance of the subcomponents. The subset, in this context, includes subcomponents that form between 30-70% of a total statistical variance of a noise-free reference ECG signal. In certain implementations, the processor receives and stores operating parameters from an external device via the wireless communication circuit, and processes the digitized ECG signals based on the stored operating parameters.

In certain implementations, the ECG signals are recorded for a time period beginning before the tactile input is received, and ending after the tactile input is received. In still other implementations, the power supply includes a battery that provides power for operating the apparatus, without replacement or recharging, for at least 30 days of continuous sensing, digitizing, and processing (e.g., to detect the arrhythmia in the digitized ECG signals). Such a long-term power approach can be made possible, for example, via the recognition and/or discovery above and implementation of subcomponent analysis.

The audio signals can be processed in a variety of manners. In some embodiments, the one or more processors carry out at least one of: identifying the presence of a human voice in the audio signal, saving the audio signal in memory, converting voice in the audio signal to text, and compressing the audio signal to reduce data volume, prior to the recorded voice being transmitted to the external device.

Various embodiments are directed to methods as may involve operation of one of more of the above-described apparatuses, as described herein. Such embodiments may, for example, involve ECG and audio detection as above, with related storage and processing, and linking audio with ECG signal recordings. The processing may involve decomposition approaches as characterized, with related communication to the subject and/or to a remote medical professional. Housings can be implemented and supported near the subjects' thorax as described, with various fastening/supporting approaches, as well as approaches to passing signals into the housing.

According to another example embodiment, an apparatus includes two or more ECG sensing electrodes, digitizing and computing circuits, a housing that houses the digitizing and computing circuits, a fastener that mechanically fastens and electrically couples the housing to one of the electrodes, and a lead wire that couples the other one(s) of the electrodes to the digitizing circuit. The electrodes adhere to remote locations on a patient and sense ECG signals therefrom, and couple the signals to the digitizing circuit via the fastener or the lead wire(s). The digitizing circuit digitizes the ECG signals, and the computing circuit processes the digitized ECG signals by one or more of removing noise, detecting an R-R interval, detecting a Q-T interval, and detecting a QRS complex.

Another example embodiment is directed to a patient-worn apparatus for recording an ECG from the patient. The apparatus includes a first circuit that digitizes an ECG signal obtained from the patient via at least two ECG leads, and a computing circuit that is connected to the first circuit to receive the digitized ECG signal. The computing circuit decomposes the digitized ECG signal into subcomponents, computes a statistical variance of the subcomponents over a time interval, and determines if one of the at least two ECG leads is disconnected from the patient based upon the statistical variance of the subcomponents. In another embodiment, detection of a disconnected ECG lead is made by computing a ratio of the variance of a subset of the subcomponents to total variance, wherein the subset includes those subcomponents that comprise 30 to 70% of the total variance of a representative clean ECG.

Another example embodiment is directed to an apparatus including a sensing electrode that adheres to and senses physiological signals from a patient, a denoising component and a fastener that fastens the denoising component to the sensing electrode. The denoising component includes a housing having a digitizing circuit, a computer circuit and a battery. The digitizing circuit digitizes the signals received via the sensing electrode and at least another sensing electrode coupled to the patient, the computing circuit processes the digitized signals to remove noise therefrom, and the battery powers the digitizing and computing circuits. The fastener mechanically fastens the housing to the sensing electrode, which supports the weight of the denoising component via the fastener while the first sensing electrode is adhered to the patient.

According to another example embodiment, physiological signals of a subject human or animal are collected, preprocessed and digitized by a telemetric ambulatory monitoring device (TAMD) that is worn by the subject. The digitized signal is denoised using one of several signal processing algorithms, a feature signal is created from the denoised signal, physiologic events are detected, and the denoised signal is compressed to reduce the data volume in order to reduce the energy required to telemeter the signal. A confidence signal is computed that provides a metric of the validity of points comprising the feature signal. An additional confidence signal is computed to evaluate the validity of detected events. The monitoring device includes a wireless communication module to communicate information to and from a data review system. Further, a process is described for detecting, classifying, and reporting arrhythmia events that provides for efficiency and accuracy.

In one aspect of this invention, a component of computing the confidence signal is a dynamic signal-to-noise ratio (dSNR) that is updated frequently, and in the case of a cardiac signal, it is updated for each cardiac cycle or portion of the cardiac cycle. Feature points extracted from the denoised signal are classified as valid or invalid and only valid features are used to compute a parameter including a mathematical combination of valid features. dSNR can also be used to identify segments of the physiologic signal that contain no useful information.

In another aspect of this invention, physiologic events are detected. A confidence signal is computed and used to classify a detected event as valid, invalid, or uncertain. Events classified as valid are accepted and included in a report summarizing arrhythmia events without the need for verification by a trained person.

In another aspect of this invention, parameters derived from valid feature points of a physiological signal are computed within the TAMD, thereby reducing the volume of data that must be transmitted, resulting in a net reduction in power consumption and hence longer battery life.

Various example embodiments are implemented as described in or otherwise in connection with the embodiments in the underlying provisional application to which benefit is claimed (U.S. Provisional Patent Application Ser. No. 61/869,250), which is fully incorporated herein by reference. For instance, various embodiments as characterized in the Appendices therein may be implemented within a housing or related component as applicable for detecting cardiac or other physiological signals as characterized in the following description and/or in the claims.

In accordance with a particular embodiment, and referring to FIG. 1, a system is comprised of an apparatus 5101 that is worn by a human or animal subject and is responsible for measuring, processing and recording the subjects ECG. This apparatus is also referred to as a "Telemetric Ambulatory Monitoring Device" (TAMD) or "recording device". In some embodiments, the recording device continuously records ECG or records clinically significant arrhythmia events, and saves the recording on a memory element located within the device. In some embodiments, the device detects and communicates clinically significant events to a communications relay device 5102. Relay 5102 may be worn by the subject or may be placed in a purse or kept nearby. Communications between the recording device 5101 and relay device 5102 can occur via a USB communications link or wireless link. Relay device 5102 receives the recording and forwards it to data collection and review system (DCRS) 5106. In some embodiments, the relay device includes a commercially available smart phone running an application that may perform some processing functions as well as capability to interrogate and program operating parameters (e.g. tachyarrhythmia and bradyarrhythmia rate thresholds) in recording device 5101. In some embodiments relay device 5102 is a cellular relay that receives the signal from recording device 5101 via a wireless communications link and forwards the data to DCRS 5106 via a cellular communications network. In some embodiments, DCRS 5106 includes a PC running an application that receives data from the relay device via a telecommunications system, processes the received data, provides a function for a human being to review the received and processed data, and creates a report to summarize the subject's condition in a manner suitable for the intended research or clinical evaluation. In some applications, recording device 5101 may communicate directly with DCRS 5106. This may be useful for providing the patient with direct access to the information provided by 5101 and 5106 and to eliminate the need for communication relay 5102. In some embodiments, direct communication to DCRS 5106 is achieved using a cellular modem. In another embodiment, a Bluetooth communication circuit located within the housing of TAMD 5101 may be used when TAMD 5101 and DCRS 5106 are in close proximity.

Figure 2:
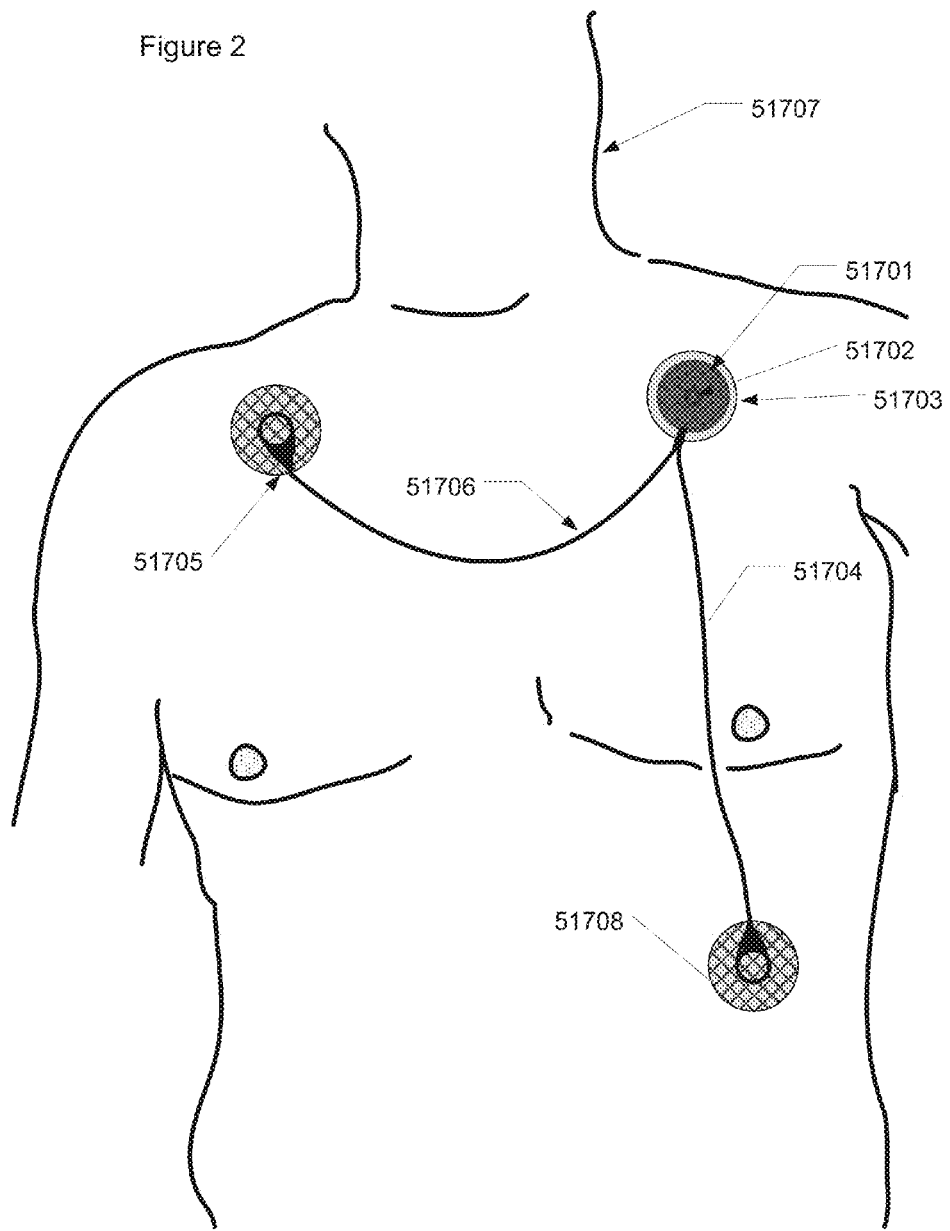
FIG. 2 shows another apparatus with a recording device integrated with a component attached to a subject's chest, in accordance with another example embodiment.

In an example embodiment, recording device 5101 is referenced in FIG. 2 as element 51701 and is shown attached to ECG sensing electrode 51703. ECG sensing electrodes 51705 and 51708 adhere to a patient for sensing ECG signals therefrom, are electrically and mechanically connected to recording device 51701. In some embodiments, recording device 51701 has a housing containing digitizing and computing circuits that process the ECG signals, and a fastener that fastens the housing to electrode 51703 and provides an electrical connection therebetween. In other embodiments, 51701 further contains a microphone and circuits to sense, digitize, and process an audio signal and one or more switches (e.g., 51702) that can be manually activated by the patient as directed by a physician when certain symptoms are felt. In one embodiment, a single switch is located on the housing. In another embodiment two switches are used, each located on opposite sides of the housing. In the latter embodiment, both switches must be pressed simultaneously to achieve activation. Upon activation of the switches, an ECG is recorded for a predetermined time span (e.g. 30 seconds prior to activating the switch and 30 seconds after) and an audio signal is recorded for 30 seconds following activation of the switch. The patient can then verbalize the nature of the symptoms immediately after activation. The audio signal saved in the memory of 51701 and forwarded to DCRS 5106 can then be used by the physician to correlate symptoms and rhythm of the patient. In one embodiment, the recording device 51701 records the ECG sensed between electrodes 51705 and 51703 and between 51703 and 51708. The electrodes are adhered to the patient using one or more of a variety of approaches, such as an adhesive applied to the electrode or an integrated adhesive pad. Electrical leads 51706 and 51704 couple the housing to each remote electrode to which the housing is not fastened. The digitizing circuit digitizes ECG signals received via the sensing electrodes, and the computing circuit processes the digitized ECG signals (e.g., to remove noise, detect an R-R interval, detect a Q-T interval, determine whether an arrhythmia is present, or evaluate repolarization characteristics).

Figure 6:
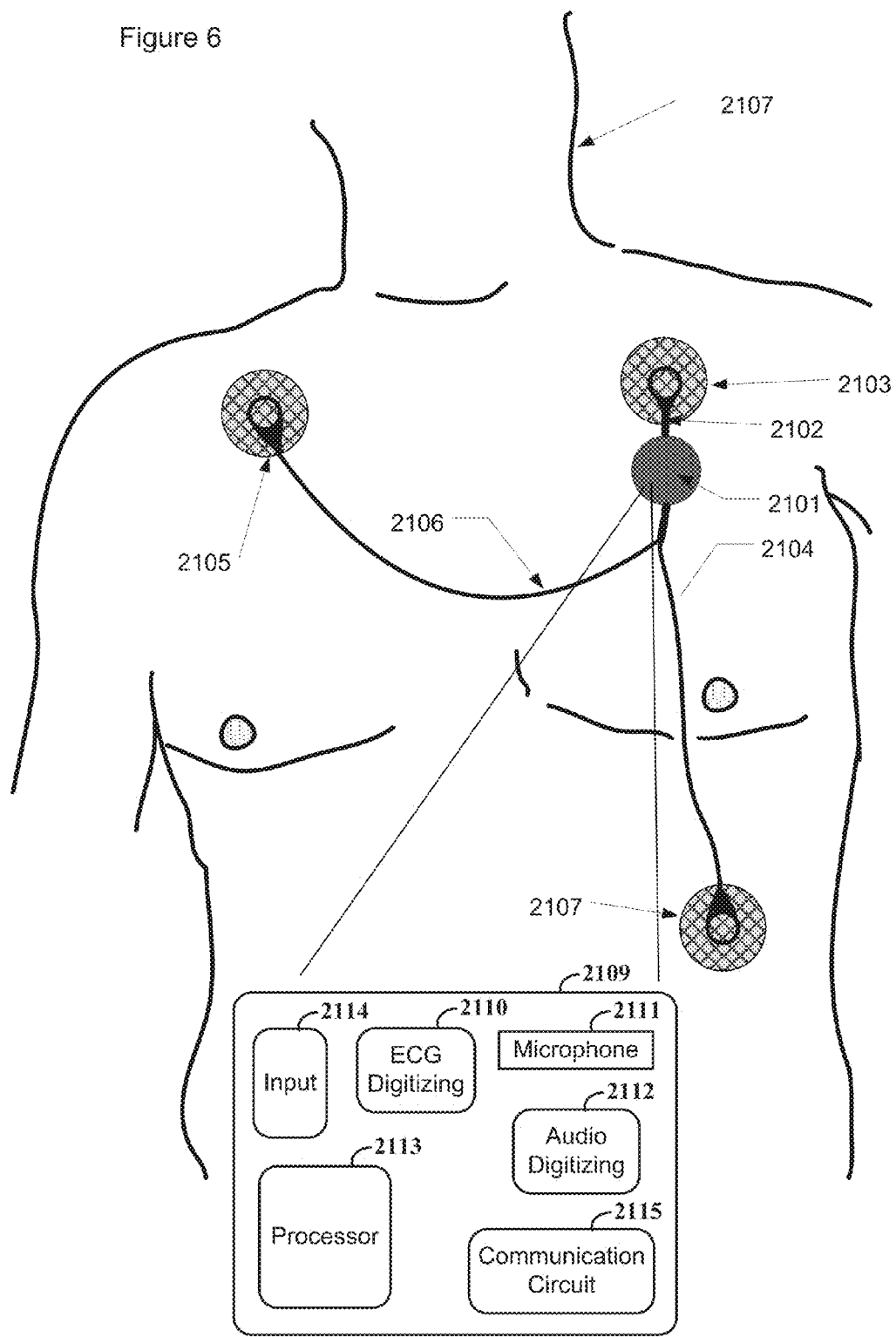
FIG. 6 shows another apparatus with ECG and audio recording devices integrated with a component attached to a subject's chest, in accordance with another example embodiment.

In another example embodiment, recording device 2101 referenced in FIG. 6 is attached to ECG skin electrode 2103 by short lead wire 2102 extending from within the housing of recording device 2101. In one embodiment lead wire 2102 is 1 to 2 cm long. ECG sensing electrodes 2103, 2105, and 2107 adhere to the patient for sensing ECG signals therefrom and are electrically connected to recording device 2101. Recording device 2101 has a housing 2109 (shown in inset) containing digitizing 2110 and computing circuits 2113 that process the ECG signals, a microphone 2111 and circuitry 2112 to sense, digitize, and process an audio signal, and a short lead wire 2102 containing a fastener that fastens the housing of recording device 2101 to electrode 2103 and provides an electrical connection therebetween. The housing 2109 also includes an input circuit 2114 for receiving a user input, and a communication circuit 2115 for communicating (e.g., wirelessly) recorded ECG and audio data to an external recipient device, and may include further circuitry and components such as a battery or transducer as discussed herein. In one embodiment housing 2109 includes an accelerometer and associated circuitry to enable recording of subject movement activity. In one embodiment, the recording device 2101 records the ECG sensed between electrodes 2105 and 2107 and between 2103 and 2105. In an alternate embodiment, 2101 records a single channel ECG sensed using electrodes 2105 and 2107. The electrodes are adhered to the patient using one or more of a variety of approaches, such as an adhesive applied to the electrode or an integrated adhesive pad. Electrical leads 2106 and 2104 electrically couple the housing to each remote electrode to which the housing is not fastened.

In various embodiments, referring to FIG. 3, a compact arrangement including housing 5301 and electrode fastener 5302 are used to mitigate or eliminate the need to couple each electrode to remote processing devices, which can be cumbersome for patient use. Such approaches may, for example, be facilitated using a signal processing approach as described and/or referenced in the Appendices noted above, to facilitate an efficient use of circuitry and/or power that, in turn, facilitates the implementation of the housing and circuitry therein in a compact and lightweight component that can be supported by a single standard ECG electrode. Such an efficient signal processing approach can further facilitate the use of low power and, in turn, a lightweight battery to supply power may also be incorporated into the housing. Accordingly, the housing, circuitry and battery can be completely supported by the electrode to which it is fastened, while the electrode is fastened to a patient. For instance, a housing 5301 having an average thickness of less than 12 mm and a volume of less than 18 cc is implemented in connection with various embodiments. In some implementations, the housing and electrode are integrated into a common component, such as by including the electrode within the housing and employing the fastener as part of the housing.

The lead wires are implemented using one or more approaches, to suit particular applications. In some embodiments, referring to FIG. 2, the flexible insulated lead wires 51704 and 51706 are greater than 10 cm in length, and in other implementations, the flexible insulated lead wires are greater than 15 cm in length. The spacing between ECG sensing electrodes is increased to improve the quality of the sensed ECG signal, for certain implementations. In still other implementations, the flexible insulated lead wires are less than 3 mm in diameter. In further implementations, the electrical leads are replaced with a wireless connection to remote electrodes, each of which is powered by an integrated battery for communicating the wireless signals. Such an approach thus entails two or more self-contained electrodes, one of which incorporates wireless receiving circuitry for coupling to remote electrodes, as well as digitizing and processing circuitry that process ECG signals obtained from the electrodes with desirable accuracy.

The computer circuitry includes one or more of a variety of types of circuits and/or modules operable to carry out one or more processing functions. In some embodiments, the computing circuit processes each digitized ECG signal by decomposing the signal into subcomponents, identifying a location of the QRS complex of a cardiac cycle in the ECG signal, identifying a first time window in the cardiac cycle that includes the QRS complex, and identifying at least one time window in the cardiac cycle that does not include the QRS complex. For each of the identified time windows, the computing circuit identifies target subcomponents as subcomponents that contain more energy that is within the band of frequencies characteristic of a desired ECG signal in the time window than energy that is outside the band of frequencies of the desired ECG signal. The computing circuit then reconstructs a denoised signal from the received ECG signal, using at least two of the identified target subcomponents. In some embodiments, the desired ECG signal is the signal present when noise sources are absent, such as when the patient is still, ECG sensing electrodes are in good condition and secured to well-prepared skin, and the area surrounding the patient is void of electromagnetic interference.

In some embodiments, processing includes detection of QRS complexes and using R-R intervals to determine if a tachyarrhythmia, bradyarrhythmia, pause, or atrial fibrillation (AF) event has occurred. Arrhythmias are detected based upon selection of criteria as one of a menu of criteria. For example, tachyarrhythmia may be defined as 6 consecutive interbeat intervals exceeding a selected rate threshold. Bradyarrhythmia may be defined as 3 consecutive interbeat intervals below a selected rate threshold. Pause may be defined as no beat detected for a period of more than 3 seconds. An AF event may be detected when the degree of variability in R-R intervals exceeds a threshold for more than 60 seconds. When an arrhythmic event is detected, the recording device captures an ECG segment and saves in memory. This segment may include a time period prior to and after occurrence of the arrhythmia, 30 seconds, for example. This is referred to as an autotrigger capture of an event.

In some embodiments the variability of R-R intervals is evaluated to determine if AF is present. In other embodiments, the atrial electrical activity is evaluated. In yet other embodiments, a combination of R-R interval characteristics and atrial electrical activity is used to determine is AF is present. If AF persists for more than a predetermined time, an AF event is detected that triggers recording of an ECG strip. Various embodiments are directed to detecting AF using one or more of the following approaches:

- Characterization of a density histogram of RR intervals or successive R-R interval differences using nonlinear statistics such as Kolmogorov-Smirnov (Tateno, Glass)
- Computing variance, root mean square of R-R intervals or successive R-R interval differences
- Evaluating R-R intervals for a segment of an ECG recording using Lorenz plots (Medtronic)
- Evaluating coherence of two adjacent segments of ECG recording (Chon)
- Evaluating mean absolute difference of consecutive R-R intervals in an ECG segment (Telectronics, Greenhut)
- Computing the ratio of consecutive R-R intervals and comparing moving averages of the ratios to a threshold (Lifewatch, Korzinov)
- Computing spectral entropy of atrial cardiac activity from an ECG and comparing to a predetermined threshold (GE, Taha)

In an alternate embodiment, multiscale entropy measurements of R-R interval dynamics is quantified for an ECG strip as described in Appendix B of the provisional application referenced above, which is fully incorporated herein by reference. In an example embodiment, entropy-based analysis is used to quantify complexity or irregularity of interval dynamics. For general information regarding entropy-based analysis, and for specific information regarding entropy-based analyses that may be implemented in accordance with one or more example embodiments, reference may be made to the Multiscale Entropy (MSE) approaches as described in M. Costa, A. L. Goldberger, and C.-K. Peng, "Multiscale Entropy Analysis of Complex Physiologic Time Series," Phys. Rev. Lett. 89, 6, (2002), which is fully incorporated herein by reference.

Figure 4A:
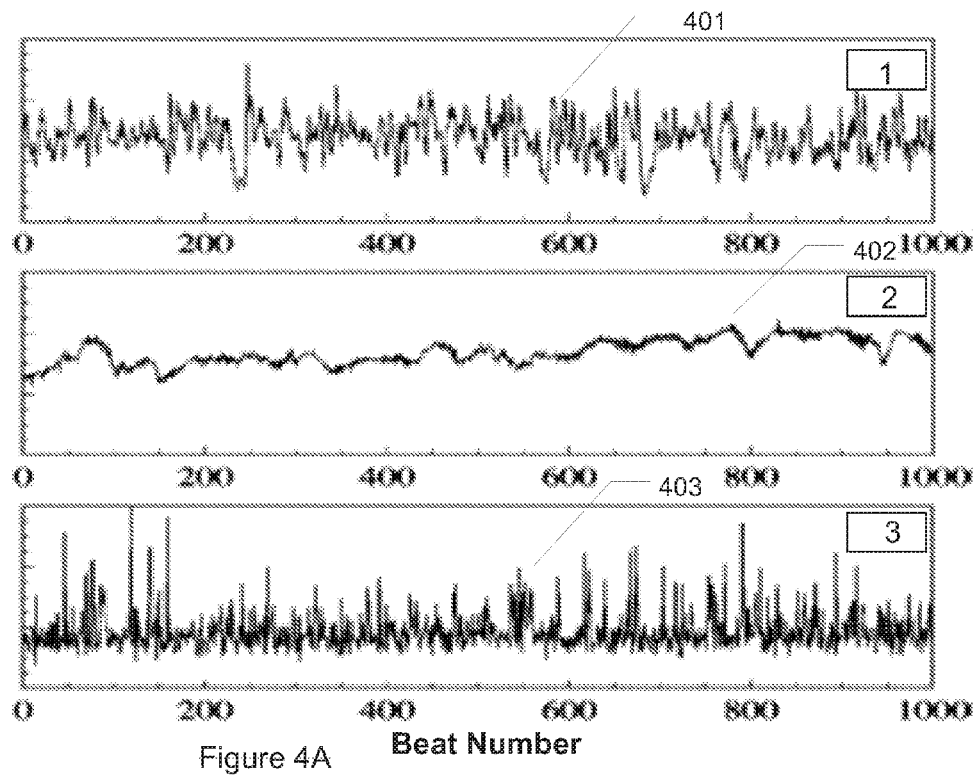
FIG. 4A shows plots that illustrate example beat-to-beat R-R interval dynamics with different characteristics as detected in accordance with one or more embodiments.
Figure 4B:
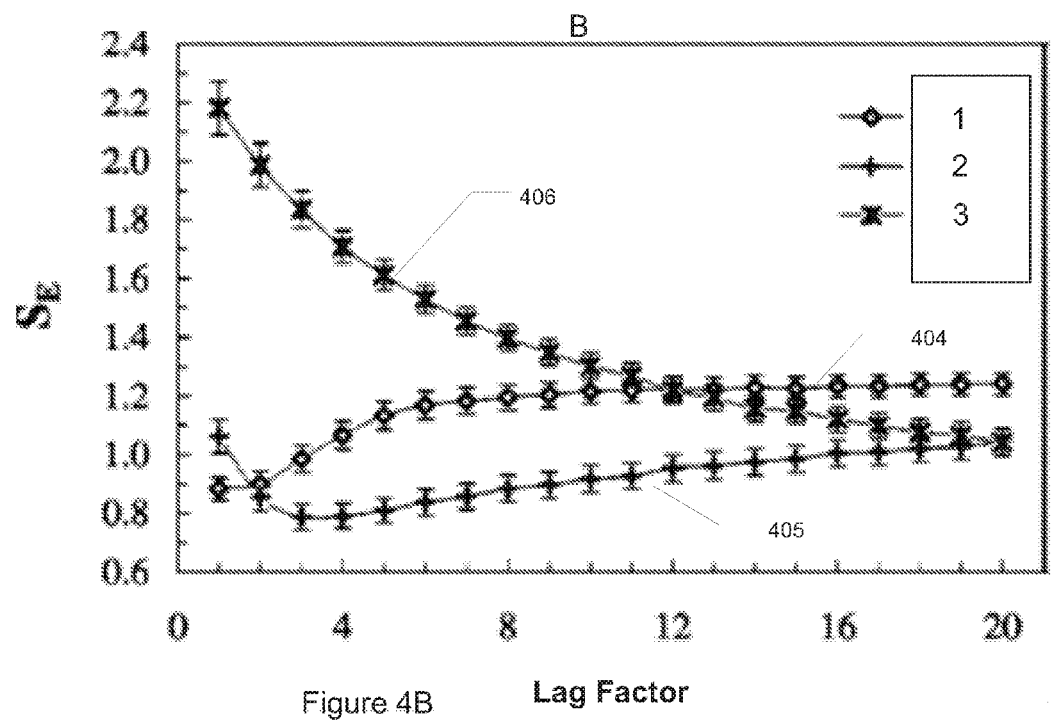
FIG. 4B shows plots pertaining to multiscale entropy (MSE) with lag factor relative to the plots shown in FIG. 4A, in accordance with one or more embodiments.

Referring to FIGS. 4A and 4B, various example embodiments involving beat-to-beat intervals are shown with respect to plots that are implemented, for example, in computing a metric indicative of the presence of AF (e.g., as may be implemented with the system shown in FIG. 1). In FIG. 4A, plots 401, 402, and 403 illustrate beat-to-beat R-R interval dynamics with different characteristics: plot 401 shows an example of high variability and high complexity (normal healthy heart); plot 402 shows an example of low variability and low complexity (diseased heart with heart failure); and plot 403 shows an example of high variability and low complexity (diseased heart with atrial fibrillation). Plots 401 and 403 in FIG. 4A are both characterized by high variability. However, plot 401 corresponds to normal dynamics of a healthy heart, and plot 403 illustrates R-R interval dynamics of a heart in atrial fibrillation. These two plots demonstrate that both the healthy and diseased heart can both be characterized by high R-R interval variability, but the presence of AF can be discriminated by assessing complexity of R-R interval dynamics.

Complexity can be quantified using tools, such as multiscale entropy (MSE), that measure system entropy at various lags. In FIG. 4B, MSE is shown for the corresponding plots 404, 405, and 406, with lags ranging from 1 to 20. In FIG. 4B, plot 404 shows MSE for plot 401 of FIG. 4A, plot 405 shows MSE for plot 402, and plot 406 shows MSE for plot 403. In some embodiments involving these examples, the MSE trend is approximated by a linear equation for the first few lags, and the offset and slope of the linear equation can be used to quantify the complexity of interval dynamics and detect AF. In an example illustrated in plot 406, the irregular RR interval dynamics with low complexity indicative of atrial fibrillation is characterized by high offset and large negative slope of the linear equation approximating multiscale entropy. In some embodiments, the MSE trend can be used to discriminate between bigeminy or trigeminy dynamics and AF. With many existing algorithms, bigeminy or trigeminy often trigger a false positive detection of AF. In an embodiment where the first few lags of the MSE trend is approximated by a linear equation, bigeminy and trigeminy are characterized by an offset and slope that is higher than is typical of AF.

Figure 5:
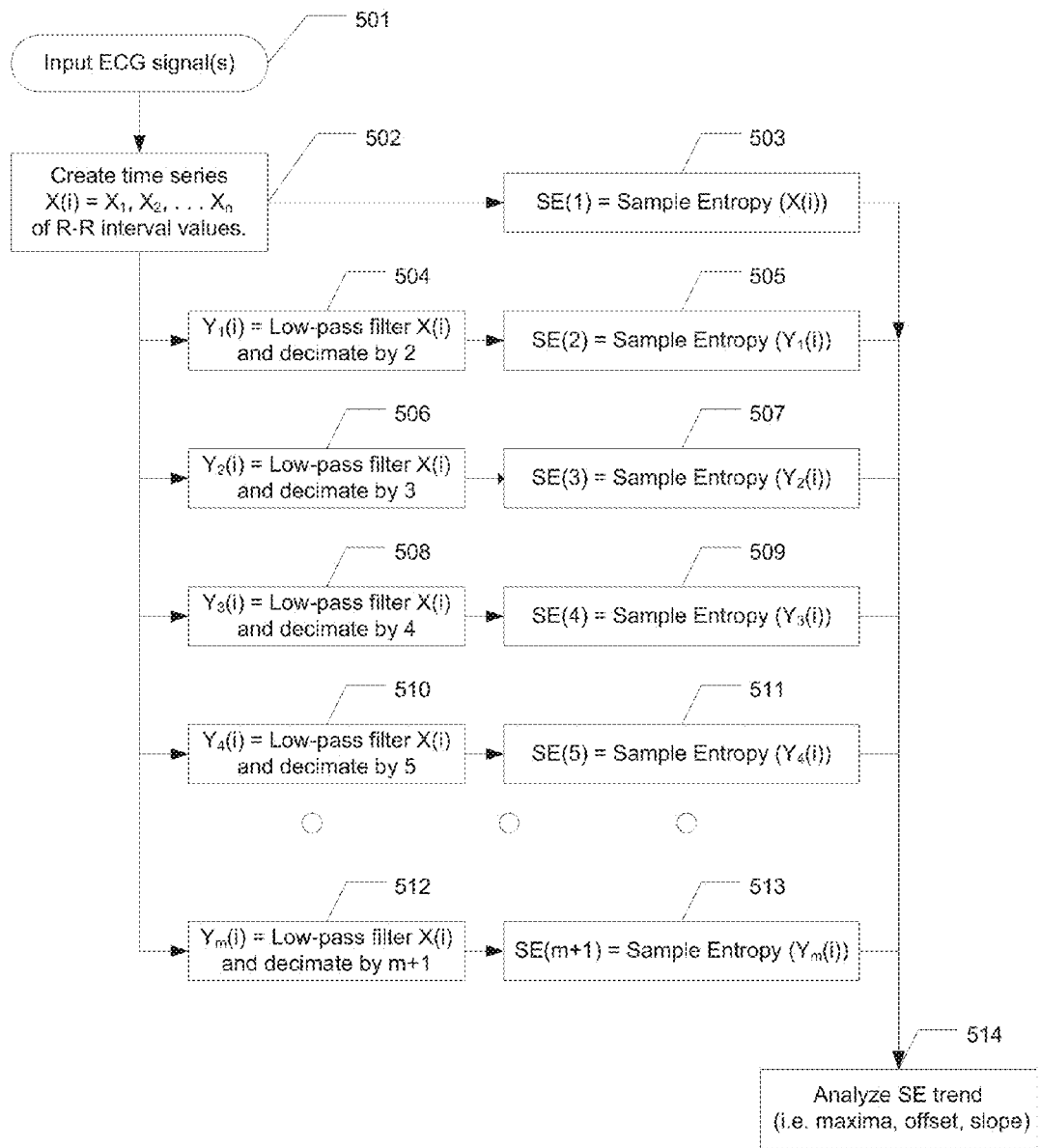
FIG. 5 shows a method for detecting atrial fibrillation, as may be implemented in accordance with one or more example embodiments.

In an example embodiment, and referring to FIG. 5, multiscale entropy (MSE) is computed and analyzed to detect atrial fibrillation. One or more ECG signals are input at 501. A time series X(i) of R-R intervals is derived from the cardiac signals in 502. Time series X(i) may include between 40 and 500 beats, although fewer or more beats may be used.

Time series X(i) is processed to compute sample entropy SE(1) in step 503. Time series X(i) is further processed to compute sample entropy at multiple lags. For example, in 504 X(i) is low pass filtered (LPF), decimated to remove every other point, and sample entropy SE(2) is computed for the resulting time series Y1(i) in step 505. In one embodiment, the frequency cutoff of the LPF is 0.5/(level of decimation). Steps 506 through 513 mirror steps 504 and 505, and in which the low-pass filter cutoff and the level of decimation are set, for example, with the LPF cutoff in 504 being ¼ and the level of decimation being 2. The level of decimation corresponds to a lag at which dynamics are evaluated and is also referred to as the scale of the entropy estimate. In 506, the LPF cutoff is ⅙ and the level of decimation is 3 (2 of every 3 points is removed). In 508, the LPF cutoff is ⅛ and the level of decimation is 4 (3 of every 4 points is removed). In one embodiment the LPF is an IIR filter such as Butterworth filter. In another embodiment the LPF is an FIR filter such as moving average filter. The number of scales (m+1) as discussed above may be implemented to suit various applications. In one embodiment, the number of scales (m+1) is 10. The resulting MSE trend of entropy values, SE(1), SE(2), SE(3), . . . SE(m+1) is analyzed to calculate maxima, slope, and offset. One or more of maxima, slope, and offset are compared to those characterizing the presence of AF. In one embodiment, a method used for compute sample entropy is the same for all scales and may be implemented in accordance with the method described in J. S. Richman and J. R. Moorman, "Physiological time-series analysis using approximate entropy and sample entropy," Am. J. Physiol. 278, H2039 (2000), which is fully incorporated by reference.

In some embodiments, the recording device includes both autotrigger and patient activated recording of an event. Recording of a patient activated event is triggered manually by the patient. In one embodiment, the patient triggers an event by squeezing the recording device between thumb and index fingers. Squeezing the recording device activates two sensors located on the surface of or inside the housing, one on each side of the recording device. Compared to triggers that require that only a single button be pressed to activate an event, squeezing reduces the incidence of false triggers as accidental activation of both sensors is less likely than for a single sensor. In various embodiments useful sensors include those that sense one or more of pressure, stress, and strain. In one embodiment, a first stationary conductive element and a second moveable conductive element are placed in proximity. The second conductive element has spring-like properties, such as beryllium copper, that allow it to deflect and make contact with the first element when force is applied to the second element. For patient activated triggers, the recording device may capture 5 minutes prior to and 2 minutes after triggering. Capturing additional time prior to activation is done in recognition of the fact that if a patient faints unexpectedly, a few minutes may need to lapse from the time of fainting until the patient regains sufficient mental faculties to activate the recording device. In another embodiment, a patient activated trigger captures an ECG signal 30 seconds prior to and 30 seconds after triggering.

In connection with various embodiments, an apparatus includes ECG sensing components together with audio components that sense audio from a patient. Such an approach may, for example, be implemented in a device package small enough to be coupled to a patient-worn electrode and supported by adhesion of the electrode to the patient. In connection with these embodiments, it has been recognized/discovered that, by detecting ECG signal events with high certainty, such a package can be implemented on small scale with low power consumption in regard to collection, processing, and transmission of data.

In a more particular ECG and audio-sensing application, a first ECG sensing electrode adheres to a patient and senses, with a second ECG sensing electrode, at least one ECG signal from the patient. A microphone senses audio (e.g., the patient's voice), and digitizing circuits receive and digitize the at least one sensed ECG signal and the sensed audio. One or more computing circuits process the digitized ECG signal by at least one of removing noise, detecting a QRS complex, assessing signal quality, and detecting arrhythmias, and process the digitized audio signal. In one embodiment the audio signal is processed by at least one of identifying the presence of a human voice, compressing the voice signal, and converting voice to text. In one embodiment audio will be captured for 30 seconds, in addition to recording ECG, upon patient event activation. The amplified output of a water-tight microphone (e.g., PUI Audio PN POW-1644-B-R) will be digitized at 8 bit resolution at an 8 kHz rate and processed by a microprocessor located with TAMD 5101. In one embodiment, recording of audio only upon identifying the presence of a human voice (i.e. voice activated recording) and compression will be accomplished with OPUS, an open-source audio and speech codec standardized by Internet Engineering Task Force in 2012 [K. Vos, et. al, Voice coding with Opus. 135th AES Convention 2013 Oct. 17-20 New York, USA.], which is fully incorporated herein by reference.

A communication circuit communicates the processed digitized ECG signals from the apparatus to a device external to the apparatus. In some embodiments, it can be useful to fasten TAMD 5101 proximal to the thorax in order to render it convenient for the patient to activate a symptomatic event recording. Such an embodiment may also be useful when recording the patient's voice, as a location proximal to the thorax is close to the patients' mouth and may improve the quality of the audio signal thereby recorded relative to placing TAMD 5101 at other locations on the body. In one embodiment, a fastener mechanically fastens the housing of 5101 containing the microphone, digitizing circuits, computing circuits and communication circuit to the first ECG sensing electrode, and electrically couples the first ECG sensing electrode to the digitizing circuit. In an alternative embodiment, the fastener includes a strap or band surrounding the thorax of the patient. The strap or band includes an elastic material to maintain a relatively fixed position on the thorax of the patient. In an alternate embodiment, the fastener includes a lanyard looped around the neck of the patient to support TAMD 5101 proximal to the thorax. In yet another embodiment, the strap or band includes an elastic material and is used both as a fastener for TAMD 5101 and for holding electrodes against the surface of the skin. In some embodiments the electrodes held in place by the strap or band are dry electrodes (i.e. electrodes that do not incorporate a gel material in contact with the skin) such as those available from Orbital Research (Cleveland, Ohio).

Various embodiments, such as those described above in connection with the sensing of audio such as a patient's voice, may be implemented in connection with embodiments shown in and described in connection with embodiments in Appendices A, B, C and D of the above-referenced provisional application. Appendix A generally corresponds to U.S. Pat. No. 9,339,202. Appendix B generally corresponds to U.S. Pat. No. 8,688,202. Appendix C includes embodiments directed to sensing and accurately reporting conditions in a research-type environment, as may be implemented in accordance with one or more approaches discussed in the other appendices, text, figures and claims. Appendix D generally corresponds to PCT Patent Application No. PCT/US2013/024770. Respective embodiments as discussed herein and in the Appendices may employ apparatuses, methods and general approaches employed in other embodiments described in these Appendices, such as for processing physiological signals. All of these documents and the Appendices, the patent documents to which they pertain and references cited therein are fully incorporated herein by reference.

Referring to FIG. 3, in some embodiments housing 5301 accommodates a microphone, at location 5308 for example, in a manner that can be used to record the subject's voice for the purpose of keeping an audio diary of patient symptoms, observations, and activities. Audio recording is implemented with various embodiments described herein, such as by implementing a small recording device located on the upper chest, fixed in position by an ECG sensing electrode. Locating the recording device close to the patient's mouth provides the audio recording with higher quality than, for example, a recording device located lower on the body. The microphone is electrically connected to amplification, filtering, and digitization electronics contained within the housing and the digitized audio signal is saved in flash memory. In some embodiments, the audio signal may be compressed using analog or digital techniques well known in the art to save memory and reduce the need for bandwidth when communicating the voice information from the recording device. In some embodiments, speech recognition may be applied to convert the voice signal to text as a means of reducing the need for information storage and transmission. In some embodiments, audio recording is initiated upon triggering of a patient activated event. In this scenario, the audio recording may be active for a few minutes (e.g. 2 to 5 minutes) to allow the patient time to verbalize the symptoms associated with the event. In other embodiments, the audio recording circuitry may remain active for several minutes following triggering of the event, but audio will only be recorded when the sound level exceeds a predetermined threshold (e.g. as in voice activated recording) or when computer processing recognizes that a human voice is speaking. This may be useful to conserve memory and reduce overall current consumption of the recording device.

In another embodiment, the audio recording may be activated upon the automatic detection of certain arrhythmic events having characteristics matching an "audio recording" criteria. The audio recording criteria may be different than the criteria used for normal event detection and recording. In one embodiment, when the recording device detects an event matching the audio recording criteria, it communicates a message to the relay device indicating that an event matching the audio recording criteria has occurred. Upon receipt of the message the relay device notifies the patient through an audible alert generated by the recording device or via the relay device. In one embodiment, the alert generated by the relay device is a ring tone. Upon responding to the ring tone, the patient can then verbalize or text the nature of any symptoms they are experiencing. This feature may be useful if a patient is forgetful about marking symptomatic events and documenting the nature of the symptoms experienced during the event. In addition to providing physicians with additional information that allows them to better understand symptom-rhythm correlation in the patient, this feature may also be useful for providing biofeedback to patients to teach them to be more perceptive of their rhythm status of their heart.

In some embodiments, detecting certain rhythm characteristics could similarly be used to trigger an audible ring or tone in the relay device or the recording device to notify the patient that certain arrhythmias are occurring. Such notification could be useful, for example, if a patient experienced a paroxysmal AF event of longer than a specified duration. When such an event occurred, the patient could take a pill to chemically arrest the AF or take a pill to initiate anticoagulation to avoid stroke. Early notification, as provided by direct notification of the patient as a result of this feature, could facilitate improved outcomes in pill-in-a-pocket approach to arrhythmia management as a result of earlier treatment. The conditions necessary to trigger notification of the patient may be different than the conditions necessary to trigger recording of an ECG strip and may often require the occurrence of an arrhythmia of greater severity.

In some embodiments, the recording device is designed to allow the device to continue operating during and following exposure to water. This can be useful to avoid damage to the device if accidently placed in a washing machine, dropped in water, or if worn while swimming, bathing, or showering. In one embodiment, the recording device includes design features that, when combined, keep the device sealed against fluid ingress. Referring again to FIG. 3, these design features include the following aspects: a) Housing 5301 fabricated of a water-proof material such as ABS plastic or HDPE. Joints are sealed, for example, with an adhesive or with ultrasonic welding to create a water-tight seal. b) Battery compartment 5306 and 5307 is round and accommodates the use of a coin cell such as the Panasonic CR2450. The battery compartment is accessed via a mating cap and is sealed with a rubber member located on the inside surface of the cap or with an O-ring to create a water-tight seal. In one embodiment, the mating cap is threaded. In another embodiment, the mating cap employs a snap mechanism to secure it to the housing. c) Access to the USB port is provided via 5 pins 5304 that extend through and are embedded in the side wall of the housing in a manner that creates a water-tight seal. The outside surface of these pins, reference 5305, is approximately flush with the surface of the housing. In one embodiment, a mating carriage contains spring-loaded conductors that make mechanical and electrical contact with these pins from the outside of the housing to facilitate USB port data transfer. d) Connection to the sensing lead wires is made via pins 5309 that extend through and are embedded in the side wall of the housing in a manner to create a water-tight seal. The pins extend into a compartment located on the periphery of the housing. A mating female connecting element located on the end of the lead wire is inserted on each pin. In one embodiment, once the lead wires are attached to the pins, a hinged element is closed and secure with a fastener element. The hinged element contains one or more features that prevent the connector from pulling off the pin. In an alternate embodiment, pins 5309 are 1.5 mm diameter and protrude into a molded extension of the housing that would serve as a mating connector for a standard DIN to snap ECG lead wire compliance with the DIN 42-802 standard.

In some embodiments, the recording device includes a microphone or accelerometer coupled to the skin and is configured and arranged to detect heart sounds for the purpose of assessing valve function, for assessing valve closure for diagnostic purposes, or for evaluating cardiac risk using an electromechanical window as described in Appendix B of the underlying provisional application. In one embodiment, the microphone is incorporated into the ECG electrode used to mechanically secure the recording device and is incorporated in a manner that facilitates contact with the skin. In this embodiment, electrical contact with the recording device circuitry can be made through a connector element located in the back side of the device housing. In other embodiments, the microphone is located at the end of a lead wire that connects to the housing in a manner similar to the ECG lead wires. To facilitate close contact with the skin, the microphone may be embedded in an adhesive-backed patch that can be adhered to the skin in a location where heart sounds can be sensed with sufficient quality to reliably detect cardiac valve activity. In various embodiments a microphone or accelerometer may be incorporated into an element for sensing vibrations emanating from inside the body in a manner described in Appendix B of the underlying provisional application.

In some embodiments, the approach shown in FIG. 18 of Appendix A of the underlying provisional application is implemented as follows. In step 1801 the ECG signal is evaluated for a segment of time (the sensing time interval) to determine if a signal is present and hence whether the leads are connected to a patient. In one embodiment of step 1801, MDSP techniques as described and/or incorporated herein are used to identify whether an ECG is present or whether it is absent or corrupt from a loose or disconnected lead. This involves decomposing the input ECG signal into subcomponents and computing statistical variance of subcomponents for the duration of the sensing time interval. In one embodiment each subcomponent center frequency corresponds to a particular frequency band of the input signal. The distribution of the variance of subcomponents (e.g., the variance of individual subcomponents over the sensing time interval) approximates the power spectral density function of the input signal. The variance of the subcomponents is compared to a threshold and if it exceeds the threshold, an ECG signal is present and the lead is connected to the patient.

In an alternate embodiment, a determination of the quality of signal is made based upon a ratio of the variance of a subset of the subcomponents to total statistical variance of the segment. A subset of subcomponents is chosen so that the subcomponents in the subset comprise a substantial portion of the total energy of a relatively noise-free representative ECG. In one embodiment, the portion in the subset is between 30 and 90%. In a related embodiment, the ratio of variance of each individual subcomponent in the subset to total variance is computed.

In some embodiment, the quality of the signal can be assessed evaluating the distribution of the ratios. In other embodiments, the quality of the signal can be assessed by evaluating the relative variance of individual subcomponents.

In other embodiments, the approaches shown in FIGS. 19 and 20 in Appendix A of the underlying provisional application are implemented for applying a distribution of subcomponent variance for detecting when an ECG signal is present (FIG. 19) and when the sensing electrodes are not connected (FIG. 20). For example, such approaches may be implemented with the above-discussed embodiments in FIGS. 1-6. Approaches for evaluating the distribution of subcomponent variance include identifying which subcomponent has the highest variance, and comparing the profile of the distribution of subcomponent variance to a profile of a known condition of the sensing leads. This technique can be applied to the signals from individual leads to determine if a single lead is disconnected, and is an alternative to using the traditional impedance measurement approach. The approach described here for step 1801 can be useful in that it can be implemented with very little power and uses fewer hardware components than traditional methods to sense lead off and hence can result in a smaller and less expensive device.

In another embodiment, the determination that a good quality signal is present is based upon computing the power spectrum of the recording in the segment using known techniques such as a Fourier transform. In one embodiment, the computed power spectrum is compared to a reference power spectrum through pattern matching or template matching. The template is formed from a reference power spectrum computed in advance or from newly acquired data from one or more representative live animals of the species and saved in memory. If the power spectrum of the segment matches the template constructed from the reference spectrum, the signal quality is deemed to be good.

In another embodiment, the computed power spectrum is evaluated by computing a ratio of power in a chosen range of frequencies that comprise a significant portion of the power in a representative noise-free ECG signal of the species to total power in the segment. In some embodiments, a significant portion of the power is considered to be more than 50% of the power in a relatively noise-free recording of the signal. In other embodiments, the energy in the chosen range of frequencies comprises 30 to 90% of the energy in a relatively noise-free representative ECG signal. For example, about 50% of the power in a relatively noise-free human ECG is in a frequency range from about 10 to 30 Hz. If the power spectrum of a human ECG is computed for a 60 second segment of a recording and the ratio of the power from 10 to 30 Hz range over the total variance (power) of the segment is computed, the ratio would normally be about 0.5. If the signal quality is poor, the ratio would be less than this.

Based upon the above discussion and illustrations, those skilled in the art will readily recognize that various modifications and changes may be made to the various embodiments without strictly following the exemplary embodiments and applications illustrated and described herein. For example, different types of signals can be captured, different types of electrodes and fasteners can be used, and a different arrangement of circuitry (e.g., fewer or more circuits) may be implemented within a housing as discussed. In addition, the various embodiments described herein may be combined in certain embodiments, and various aspects of individual embodiments may be implemented as separate embodiments. Such modifications do not depart from the true spirit and scope of various aspects of the invention, including aspects set forth in the claims.

What is claimed is:

1. An apparatus comprising:
    first and second electrodes configured and arranged to sense ECG signals from a subject; and
    an circuitry including:
        a digitizing circuit configured and arranged to receive and digitize the ECG signals sensed by the electrodes;
        an audio circuit including a microphone configured and arranged to capture voice sounds from the subject traveling through air, the audio circuit being configured and arranged to convert the captured voice sounds into electrical audio signals that can be reproduced for regenerating the voice sounds and therein providing audibly discernable speech;
        a processing circuit configured and arranged with the electrodes and digitizing circuit to digitize the ECG signals and to process each digitized ECG signal by at least one of: removing noise from the digitized ECG signal, storing the digitized ECG signal in a memory circuit, detecting a QRS complex in the digitized ECG signal, evaluating quality of the digitized ECG signal, and detecting arrhythmia in the digitized ECG signal;
        an input circuit configured and arranged to receive an input from the subject and including at least one manual switch configured and arranged to provide the input in response to the subject manually activating the at least one switch, the processing circuit and audio circuit being respectively configured and arranged with the input circuit to initiate recording of at least one of the ECG signals and the sound in response to the input; and
        a communication circuit configured and arranged to communicate the processed digitized ECG signals and the audio signals for receipt by an external device.

2. The apparatus of claim 1, further including the memory circuit, wherein the processing circuit is configured and arranged to
    store, in the memory circuit, data that represents and links the at least one of the ECG signals and the sound recorded in response to the input, thereby linking each captured ECG signal with sound recorded in connection with the captured ECG signal, and
communicate the stored data that represents and links ECG signals with recorded sound, via the communication circuit.

3. The apparatus of claim 1, further including a transducer configured and arranged to generate audible sound, wherein the processing circuit is configured and arranged to evaluate signal quality of the digitized ECG signal and to audibly communicate an indication of the evaluated quality of the signal via the transducer.

4. The apparatus of claim 1, wherein the processing circuit is configured and arranged to evaluate the signal quality of the digitized ECG signal by:
  decomposing the digitized ECG signal into subcomponents,
  computing a statistical variance of the subcomponents over a time interval, and
  assessing signal quality based upon the statistical variance of the subcomponents.

5. The apparatus of claim 1, wherein the processing circuit is configured and arranged to remove noise from the digitized ECG signal by
  decomposing the signal into subcomponents;
  identifying a location of the QRS complex of a cardiac cycle in the ECG signal;
  identifying a first time window in the cardiac cycle that includes the QRS complex;
  identifying at least one time window in the cardiac cycle that does not include the QRS complex;
  for each of the identified time windows, identifying target subcomponents as subcomponents that contain more energy that is within a band of frequencies characteristic of a desired ECG signal in the time window than energy that is outside the band of frequencies characteristic of the desired ECG signal; and
  reconstructing a denoised physiological signal using at least two of the identified target subcomponents.

6. The apparatus of claim 1 further including a housing that includes the digitizing circuit, audio circuit, processing circuit and communication circuit, the housing being constructed primarily of a non-conductive material and having at least one conductive pin embedded into the non-conductive material and configured and arranged to electrically conduct the sensed ECG signals from outside the housing to the digitizing circuit within the housing, the at least one conductive pin being sealed within and configured and arranged with the non-conductive exterior to prevent penetration of fluid into the housing.

7. The apparatus of claim 6, further including a fastener configured and arranged to mechanically support the housing proximate the subject's thorax.

8. The apparatus of claim 7, wherein
  the processing circuit is configured and arranged to detect and identify cardiac signals selected from the group of: a QRS complex, cardiac arrhythmia and a combination thereof,
  the fastener includes the first electrode and is configured and arranged to adhere to the subject's skin,
  the housing includes a conductive snap at an outer surface thereof; and
  the fastener includes a conductive snap that is configured and arranged to mate with the conductive snap in the housing, and to provide both mechanical support for the housing and electrical connection from the first electrode to the digitizing circuit contained within the housing.

9. The apparatus of claim 7,
  wherein the fastener includes the first electrode and is configured and arranged to adhere to the subject's skin,
  further including a conductive lead wire that extends through the housing, and a conductive snap connected to the conductive lead wire; and
  wherein the fastener includes a conductive snap that is configured and arranged to
    mate with the conductive snap connected to the conductive lead wire, and
    provide both mechanical support for the housing and electrical connection from the first electrode to the digitizing circuit contained within the housing.

10. The apparatus of claim 1,
  wherein the communication circuit includes a wireless communication circuit configured and arranged to wirelessly transmit data characterizing the processed digitized ECG signals and the audio signals to the external device;
  wherein the input is a tactile input from the subject and the input circuit is configured and arranged to convert the tactile input to an input signal;
  wherein the processing circuit is configured and arranged with the electrodes, digitizing circuit, and communication circuit to:
    in response to each input, record the digitized ECG signal sensed from the subject via the electrodes, and record the subject's voice via the audio circuit, and
    wirelessly transmit the recorded voice and digitized ECG signal to the external device via the wireless communication circuit, thereby providing access to ECG signals and the subject's voice as recorded in conjunction with each ECG signal recorded in response to tactile input from the subject;
  further including:
    a power supply configured and arranged to provide power to the digitizing circuit, the audio circuit, the communication circuit, the input circuit, and the processing circuit;
    a housing that houses at least the input circuit, audio circuit, communication circuit, power supply and the processing circuit; and
    a mechanical support structure configured and arranged to support the housing proximate the subject's thorax.

11. The apparatus of claim 10 wherein
  the housing is constructed primarily of a non-conductive material,
  at least one conductive pin is embedded into the non-conductive material and configured and arranged to electrically conduct a sensed ECG signal from the electrodes outside the housing to the digitizing circuit, and
  the at least one conductive pin is sealed within and configured with the non-conductive material to prevent penetration of fluid into the housing.

12. The apparatus of claim 10, further including a transducer configured and arranged to generate audible sound, wherein the processing circuit is configured and arranged to evaluate signal quality of the digitized ECG signal and to audibly communicate an indication of the evaluated quality of the signal via the transducer.

13. The apparatus of claim 12, wherein the processing circuit is configured and arranged to evaluate the signal quality of the digitized ECG signal by:
  decomposing the digitized ECG signal into subcomponents, computing a statistical variance of the subcomponents over a time interval, and assessing signal quality based upon the statistical variance of the subcomponents.

14. The apparatus of claim 10, wherein the processing circuit is configured and arranged to evaluate the signal quality of the digitized ECG signal by:

decomposing the digitized ECG signal into subcomponents, computing a statistical variance of the subcomponents over a time interval, and assessing signal quality based upon the statistical variance of the subcomponents.

15. The apparatus of claim 14, wherein the processing circuit is configured and arranged to determine whether one of the at first and second electrodes is disconnected from the subject based upon a ratio of the statistical variance of a subset of the subcomponents to total statistical variance of the subcomponents, the subset including subcomponents that form between 30-70% of the total statistical variance of a noise-free reference ECG signal.

16. The apparatus of claim 10, wherein the processing circuit is configured and arranged to receive and store operating parameters from an external device via the wireless communication circuit, and to process the digitized ECG signal based on the stored operating parameters.

17. The apparatus of claim 10, further including a memory circuit in the housing, the processing circuit being configured and arranged to store sets of data in the memory circuit, each set of data representing and linking a recorded ECG signal with sound recorded in response to the input signal, wherein the processing circuit is configured and arranged to transmit the sets of data to the external device via the wireless communication circuit.

18. The apparatus of claim 10, wherein the digitizing circuit is configured and arranged to digitize the sensed ECG signal by actively digitizing sensed ECG signals over a period of time, and the processing circuit is configured and arranged with the input device to record the digitized ECG signal by, in response to receiving the tactile input, record ECG signals sensed for a time period beginning before the tactile input is received, and ending after the tactile input is received.

19. The apparatus of claim 10, wherein the processing circuit is configured and arranged to detect arrhythmia in each digitized ECG signal, and wherein the power supply includes a battery configured and arranged to provide power for operating the apparatus, without replacement or recharging, for at least 30 days of continuous sensing, digitizing, and processing to detect the arrhythmia in the digitized ECG signals.

20. The apparatus of claim 10, wherein the mechanical support structure includes an elastic member that encircles at least a portion the thorax and is configured and arranged to hold at least one of the first and second electrodes in contact with the skin.

21. The apparatus of claim 10, wherein the mechanical support structure includes one of a loop or band configured and arranged to encircle the subject's thorax, or a lanyard configured and arranged to encircle the subject's neck.

22. The apparatus of claim 10, further including a transducer configured and arranged to generate audible sound, wherein the processing circuit is configured and arranged to process the digitized ECG signal by detecting the arrhythmia in the digitized ECG signal, and to notify the subject that an arrhythmia has occurred and to prompt the subject to verbally describe symptoms by generating sound via the transducer.

23. The apparatus of claim 10, wherein the processing circuit is configured and arranged to process each electrical audio signal by at least one of: identifying the presence of a human voice in the audio signal, saving the audio signal in memory, converting voice in the audio signal to text, and compressing the audio signal to reduce data volume, prior to the recorded voice being transmitted to the external device.

24. An apparatus comprising:

first and second electrodes configured and arranged to sense ECG signals from a subject; and an circuitry including:

a digitizing circuit configured and arranged to receive and digitize the ECG signals sensed by the electrodes;

an audio circuit configured and arranged to capture sounds from the subject and to convert the sound into electrical audio signals;

a processing circuit configured and arranged with the electrodes and digitizing circuit to digitize the ECG signals and to process each digitized ECG signal, by evaluating the quality of the digitized ECG signal and providing an indication that at least one of the first and second electrodes is disconnected from the subject, and placing the apparatus in a low power mode in response thereto;

an input circuit configured and arranged to receive an input from the subject, the processing circuit and audio circuit being respectively configured and arranged with the input circuit to initiate recording of at least one of the ECG signals and the sound in response to the input; and a communication circuit configured and arranged to communicate the processed digitized ECG signals and the audio signals for receipt by an external device.

25. A method comprising:

sensing ECG signals from a subject via first and second electrodes; and within a housing constructed primarily of a non-conductive material, receiving and digitizing the ECG signals sensed by the electrodes via a digitizing circuit;

using an audio circuit, capturing sounds from the subject and converting the sound into electrical audio signals;

in a processing circuit operable with the electrodes and digitizing circuit, digitizing the ECG signals and processing each digitized ECG signal by at least one of: removing noise from the digitized ECG signal, storing the digitized ECG signal in a memory circuit, detecting a QRS complex in the digitized ECG signal, evaluating quality of the digitized ECG signal, and detecting arrhythmia in the digitized ECG signal;

in response to receiving an input from the subject via an input circuit, recording at least one of the ECG signals and the sound via the processing circuit and the audio circuit;

communicating each processed digitized ECG signal and a corresponding one of the audio signals, via a communication circuit, for receipt by an external device; and supporting the housing near the subject's thorax.

26. The method of claim 25, wherein
processing each digitized ECG signal includes storing data that represents and links the at least one of the ECG signals and the sound recorded in response to the input, thereby linking each captured ECG signal with sound recorded in connection with the captured ECG signal, and
communicating the processed digitized ECG signals includes communicating the stored data that represents and links ECG signals with recorded sound.

27. The method of claim 25, wherein processing each digitized ECG signal includes evaluating signal quality of the digitized ECG signal, further including audibly communicating an indication of the evaluated quality of the signal using a transducer.

28. The method of claim 25, wherein processing each digitized ECG signal includes removing noise from the digitized ECG signal by
decomposing the signal into subcomponents;
identifying a location of the QRS complex of a cardiac cycle in the ECG signal;
identifying a first time window in the cardiac cycle that includes the QRS complex;
identifying at least one time window in the cardiac cycle that does not include the QRS complex;
for each of the identified time windows, identifying target subcomponents as subcomponents that contain more energy that is within a band of frequencies characteristic of a desired ECG signal in the time window than energy that is outside the band of frequencies characteristic of the desired ECG signal; and
reconstructing a denoised physiological signal using at least two of the identified target subcomponents.

29. The method of claim 25, wherein supporting the housing near the subject's thorax includes snapping the housing to a fastener adhered to the subject's skin and using the fastener to provide both mechanical support for the housing and electrical connection from the first electrode to the digitizing circuit contained within the housing.

30. The method of claim 25, wherein the housing has at least one conductive pin embedded into the non-conductive material, further including using the at least one conductive pin to couple the digitizing circuit to the first and second electrodes.

31. The method of claim 25, wherein processing each digitized ECG signal includes evaluating the quality of the digitized ECG signal by providing an indication that at least one of the first and second electrodes is disconnected from the subject, and by processing circuit in a low power mode in response thereto.

32. A method comprising:
sensing ECG signals from a subject via first and second electrodes;
receiving and digitizing the ECG signals sensed by the electrodes via a digitizing circuit;
using an audio circuit, capturing sounds from the subject and converting the sound into electrical audio signals;
in a processing circuit operable with the electrodes and digitizing circuit, digitizing the ECG signals and processing each digitized ECG signal, wherein processing each digitized ECG signal includes evaluating the signal quality of the digitized ECG signal by:
decomposing the digitized ECG signal into subcomponents,
computing a statistical variance of the subcomponents over a time interval, and
assessing signal quality based upon the statistical variance of the subcomponents;
in response to receiving an input from the subject via an input circuit, recording at least one of the ECG signals and the sound via the processing circuit and the audio circuit; and
communicating each processed digitized ECG signal and a corresponding one of the audio signals, via a communication circuit, for receipt by an external device.

* * * * *

UNITED STATES PATENT AND TRADEMARK OFFICE
CERTIFICATE OF CORRECTION

PATENT NO. : 9,492,096 B2
APPLICATION NO. : 14/467957
DATED : November 15, 2016
INVENTOR(S) : Brockway et al.

It is certified that error appears in the above-identified patent and that said Letters Patent is hereby corrected as shown below:

In the Specification

Column 1, Line 3, Insert the following after the Title:
--STATEMENT REGARDING FEDERALLY SPONSORED RESEARCH AND DEVELOPMENT
This invention was made with government support under grant numbers R44DA011815 and R43HL110739 awarded by the National Institutes of Health. The government has certain rights in the invention.--

Signed and Sealed this
Eleventh Day of March, 2025

Coke Morgan Stewart
*Acting Director of the United States Patent and Trademark Office*